(12) United States Patent
Nakayama (10) Patent No.: US 11,043,524 B2
(45) Date of Patent: Jun. 22, 2021

(54) DEVICE-BONDED BODY, IMAGE PICKUP MODULE, ENDOSCOPE AND METHOD FOR MANUFACTURING DEVICE-BONDED BODY

(71) Applicant: OLYMPUS CORPORATION, Tokyo (JP)

(72) Inventor: Takashi Nakayama, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 262 days.

(21) Appl. No.: 16/411,693

(22) Filed: May 14, 2019

(65) Prior Publication Data
US 2019/0273110 A1    Sep. 5, 2019

Related U.S. Application Data (63) Continuation of application No. PCT/JP2016/084097, filed on Nov. 17, 2016.

(51) Int. Cl.
*H01L 21/44*        (2006.01)
*H01L 27/146*       (2006.01)
(Continued)

(52) U.S. Cl.
CPC ...... *H01L 27/14636* (2013.01); *A61B 1/0011* (2013.01); *A61B 1/05* (2013.01); *H01L 24/11* (2013.01); *H01L 24/13* (2013.01); *H01L 24/16* (2013.01); *H01L 24/81* (2013.01); *H01L 27/1469* (2013.01); *H01L 27/14618* (2013.01); *H01L 27/14634* (2013.01); *H01L 24/29* (2013.01); *H01L 24/32* (2013.01); *H01L 24/73* (2013.01); *H01L 24/83* (2013.01);
(Continued)

(58) Field of Classification Search
None
See application file for complete search history.

(56) References Cited

U.S. PATENT DOCUMENTS

| | | | |
|---|---|---|---|
| 6,429,453 B1 * | 8/2002 | Park | H01L 22/20 257/48 |
| 6,797,603 B2 * | 9/2004 | Murayama | H01L 24/97 257/E25.013 |

(Continued)

FOREIGN PATENT DOCUMENTS

| | | |
|---|---|---|
| EP | 1156520 A1 | 11/2001 |
| EP | 1195806 A2 | 4/2002 |

(Continued)

OTHER PUBLICATIONS

International Search Report dated Feb. 14, 2017 issued in PCT/JP2016/084097.

*Primary Examiner* — Hung K Vu
(74) *Attorney, Agent, or Firm* — Scully, Scott, Murphy & Presser, P.C.

(57) ABSTRACT

A device-bonded body includes: a first device where a plated bump is disposed; a second device where a bonding electrode bonded to the plated bump is disposed; and a sealing layer made of NCF or NCP, the sealing layer being disposed between the first device and the second device and including filler particles made of inorganic material; wherein a surface of the plated bump includes a first area and a second area higher than the first area; and at least a part of a side surface of an outer circumferential portion of the second area intersects with a surface of the first area.

8 Claims, 6 Drawing Sheets

(51) Int. Cl.
*A61B 1/00* (2006.01)
*A61B 1/05* (2006.01)
*H01L 23/00* (2006.01)

(52) U.S. Cl.
CPC .............. *H01L 2224/02166* (2013.01); *H01L 2224/05567* (2013.01); *H01L 2224/1147* (2013.01); *H01L 2224/11462* (2013.01); *H01L 2224/12105* (2013.01); *H01L 2224/13015* (2013.01); *H01L 2224/13019* (2013.01); *H01L 2224/13026* (2013.01); *H01L 2224/13027* (2013.01); *H01L 2224/13082* (2013.01); *H01L 2224/13144* (2013.01); *H01L 2224/13147* (2013.01); *H01L 2224/13155* (2013.01); *H01L 2224/16145* (2013.01); *H01L 2224/2929* (2013.01); *H01L 2224/29386* (2013.01); *H01L 2224/325* (2013.01); *H01L 2224/32145* (2013.01); *H01L 2224/73204* (2013.01); *H01L 2224/81141* (2013.01); *H01L 2224/81191* (2013.01); *H01L 2224/81193* (2013.01); *H01L 2224/81205* (2013.01); *H01L 2224/831* (2013.01); *H01L 2224/8385* (2013.01); *H01L 2224/83192* (2013.01); *H01L 2224/9211* (2013.01)

(56) References Cited

U.S. PATENT DOCUMENTS

| 6,926,796 | B1 | 8/2005 | Nishida et al. |
| 7,528,487 | B2* | 5/2009 | Imai .................. H01L 24/13 |
| | | | 257/737 |
| 2002/0060904 | A1* | 5/2002 | Higuchi ............... H05K 3/4617 |
| | | | 361/760 |
| 2002/0072149 | A1 | 6/2002 | Yoshida |

FOREIGN PATENT DOCUMENTS

| JP | 2000286297 | A | 10/2000 |
| JP | 2002110715 | A | 4/2002 |
| JP | 2003023022 | A | 1/2003 |
| JP | 2015217162 | A | 12/2015 |
| JP | 2016141739 | A | 8/2016 |
| WO | 200045430 | A1 | 8/2000 |

* cited by examiner

DEVICE-BONDED BODY, IMAGE PICKUP MODULE, ENDOSCOPE AND METHOD FOR MANUFACTURING DEVICE-BONDED BODY

CROSS REFERENCE TO RELATED APPLICATION

This application is a continuation application of PCT/JP2016/084097 filed on Nov. 17, 2016, the entire contents of which are incorporated herein by this reference.

BACKGROUND OF THE INVENTION

1. Field of the Invention

Embodiments of the present invention relate to a device-bonded body in which first and second devices are bonded via plated bumps, and sealing resin including filler particles is filled between the first and second devices, an image pickup module including the device-bonded body, an endoscope including the image pickup module and a method for manufacturing the device-bonded body.

2. Description of the Related Art

As a technique for electrically connecting a semiconductor device to another device or the like, wiring by a wire bonding method has been performed. However, in order to respond to increase in pins and decrease in pitch in a semiconductor device, a flip chip method has been put to practical use. In the flip chip method, bumps (metal protrusions) are disposed on electrodes of a semiconductor device, and the electrodes are bonded to electrodes of another device via the bumps. In order to improve reliability of bonding, sealing resin is disposed on a bonding portion.

In the case of disposing the sealing resin after bonding, "an injection method" in which a capillary phenomenon is used to inject liquid resin into a gap of the bonding portion is used.

"A first-in method", in which film-like sealing material called NCF (non-conductive film) or liquid sealing material called NCP (non-conductive paste) is applied on a bonding surface before bonding, and thermocompression bonding is performed after that, is considered. The first-in method is better in workability than the injection method.

As disclosed in Japanese Patent Application Laid-Open Publication No. 2016-141739, filler particles made of inorganic material such as silica filler particles are included in NCF and NCP for improvement of reliability.

As disclosed in Japanese Patent Application Laid-Open Publication No. 2003-23022, there is a recess portion on a center portion of a surface of a plated bump.

SUMMARY OF THE INVENTION

A device-bonded body of an embodiment includes a first device where a plated bump is disposed, a second device where a bonding electrode bonded to the plated bump is disposed, and a sealing layer made of NCF or NCP, the sealing layer being disposed between the first device and the second device and including filler particles made of inorganic material, a surface of the plated bump including a first area and a second area higher than the first area, and at least a part of a side surface of an outer circumferential portion of the second area intersecting with a surface of the first area.

An image pickup module of another embodiment includes a device-bonded body, the device-bonded body including a first device where a plated bump is disposed, a second device where a bonding electrode bonded to the plated bump is disposed, and a sealing layer made of NCF or NCP, the sealing layer being disposed between the first device and the second device and including filler particles made of inorganic material, a surface of the plated bump including a first area and a second area higher than the first area, and at least a part of a side surface of an outer circumferential portion of the second area intersecting with a surface of the first area.

An endoscope of still another embodiment includes a device-bonded body, a wiring board connected to the device-bonded body and a signal cable connected to the wiring board, the device-bonded body including a first device where a plated bump is disposed, the first device being an image pickup device, a second device where a bonding electrode bonded to the plated bump are disposed, and a sealing layer made of NCF or NCP, the sealing layer being disposed between the first device and the second device and including filler particles made of inorganic material, a surface of the plated bump including a first area and a second area higher than the first area, and at least a part of a side surface of an outer circumferential portion of the second area intersecting with a surface of the first area.

A method for manufacturing a device-bonded body of still another embodiment includes a process for disposing a plated bump on a first device, a process for disposing a bonding electrode on a second device, and a process for bonding the plated bump of the first device and the bonding electrode of the second device via a sealing layer made of NCF or NCP, the sealing layer including filler particles made of inorganic material, a surface of the plated bump including a first area and a second area higher than the first area, and at least a part of a side surface of an outer circumferential portion of the second area intersecting with a surface of the first area.

DETAILED DESCRIPTION OF THE PREFERRED EMBODIMENTS

First Embodiment

Figure 1:
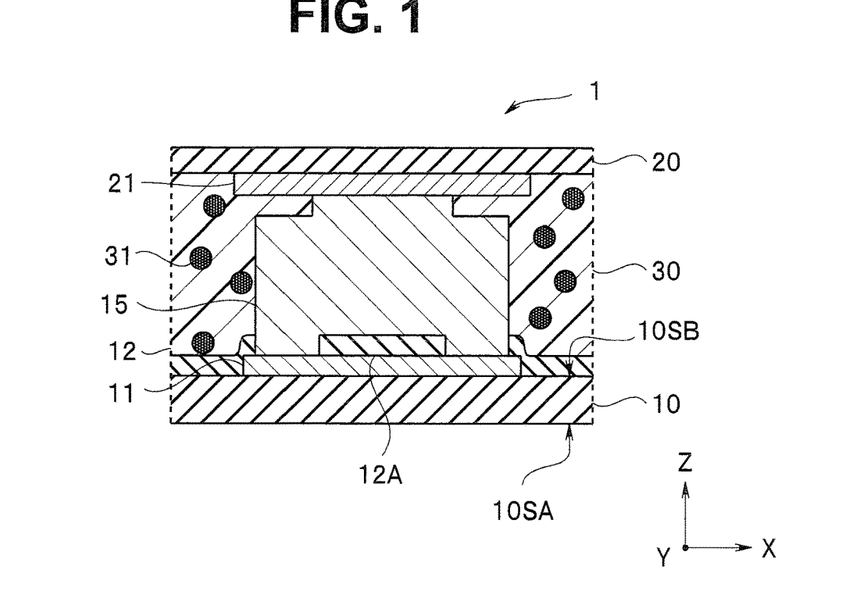
FIG. 1 is a cross-sectional view of a bonding portion of a device-bonded body of a first embodiment.
Figure 2:
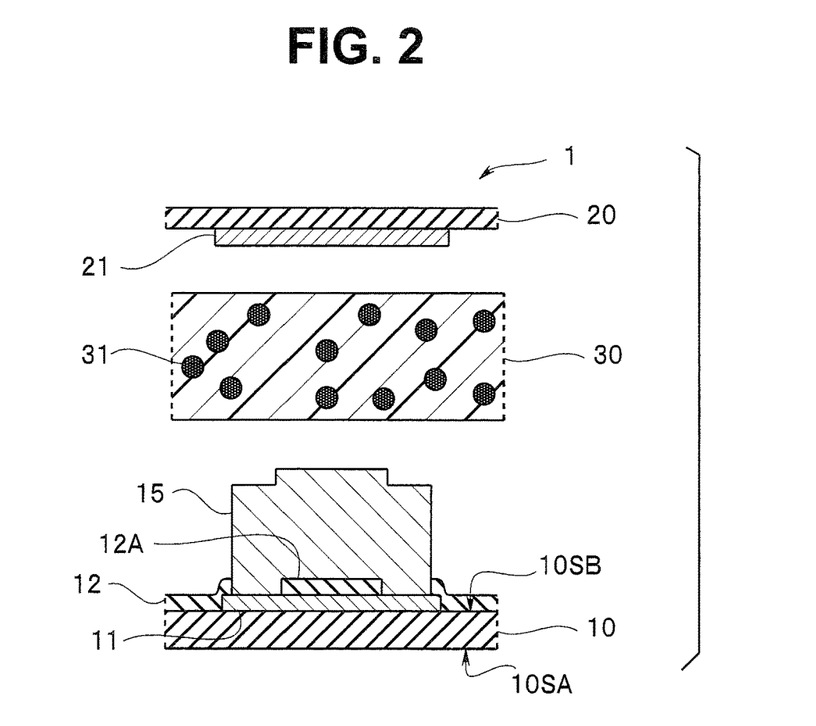
FIG. 2 is a cross-sectional exploded view of the bonding portion of the device-bonded body of the first embodiment.

As shown in FIGS. 1 and 2, a device-bonded body 1 of the present embodiment has a first device 10, a second device 20 and a sealing layer 30.

Note that it should be noticed that, in description below, drawings based on each embodiment are schematic, and a relationship between thickness and width of each portion, a thickness ratio and relative angles among respective portions and the like are different from actual ones; and, among the drawings, portions having a different mutual dimensional relationship or ratio may be included. A part of components, for example, a seed layer 18 (see FIG. 5A) may be omitted from the drawings.

Note that the device-bonded body 1 is fabricated by cutting a bonded wafer obtained by bonding a first wafer including a plurality of first devices and a second wafer including a plurality of second devices. A first device 10 and a second device 20 are bonded via a plurality of bumps 15. In diagrams below, however, only one bump bonding portion may be shown.

The first device 10 is an image pickup device made of a semiconductor and has a light receiving portion 16 (see FIG. 10) on a light receiving surface 10SA. On a back surface 10SB facing the light receiving surface 10SA of the first device 10, a plurality of base electrodes 11 electrically connected to the light receiving portion via through wires (not shown) are disposed. Plated bumps 15 (hereinafter referred to as "bumps 15") are disposed on the base electrodes 11.

The second device 20 is a semiconductor device having a signal processing circuit. On a counter-surface facing the first device 10 of the second device 20, a plurality of bonding electrodes 21 are disposed. The bonding electrodes 21 are bonded to the base electrodes 11 via the bumps 15.

The sealing layer 30 is disposed between the first device 10 and the second device 20. The sealing layer 30 is made of NCF (non-conductive film) or NCP (non-conductive paste) which is sealing material including filler particles 31 made of inorganic material. The sealing layer 30 is disposed between the first device 10 and the second device 20 by "the first-in method".

Figure 3:
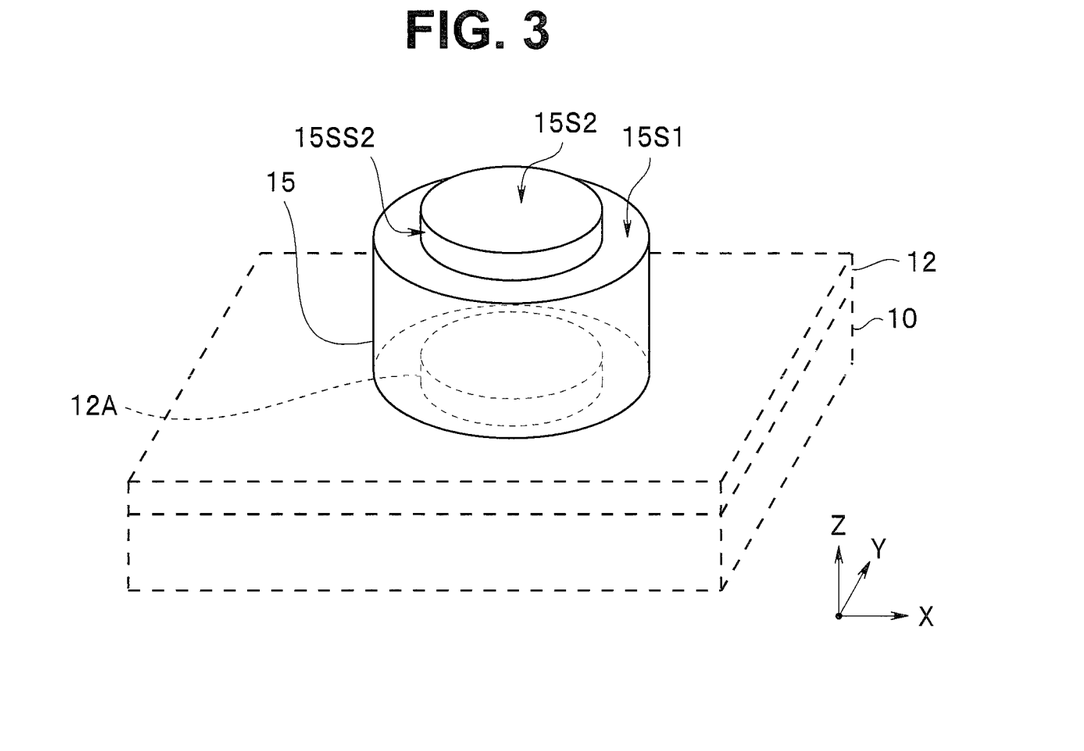
FIG. 3 is a perspective view of a bump of a first device of the device-bonded body of the first embodiment.

As shown in FIG. 3, in the device-bonded body 1 of the present embodiment, a surface of each of the bumps 15 of the first device 10 includes a first area 15S1 and a second area 15S2 higher than the first area 15S1. The second area 15S2 in a circular shape is surrounded by the first area 15S1 in an annular shape without a gap. That is, an outer circumferential portion of the second area 15S2 is in contact with the first area 15S1. More strictly, a side surface 15SS2 of the outer circumferential portion of the second area 15S2 intersects with a surface of the first area 15S1.

In the device-bonded body 1, the bumps 15 of the first device 10 and the bonding electrodes 21 of the second device 20 are bonded via the sealing layer 30 made of NCF or NCP by "the first-in method". Therefore, the method for fabricating the device-bonded body 1 has good workability. Though the sealing layer 30 made of NCF or NCP includes the filler particles 31, the device-bonded body 1 has the bumps 15 having a characteristic surface shape. Therefore, there are few filler particles 31 caught in a bonding interface, and the device-bonded body 1 is highly reliable.

<Method for Manufacturing Device-Bonded Body>

Next, a method for manufacturing the device-bonded body 1 will be described.

Although not shown, a first wafer 10W including a plurality of first devices 10 is made of silicone, and a plurality of light receiving portions are formed on the light receiving surface 10SA. The light receiving portions are CCD or CMOS sensors or the like. The first wafer 10W may be made of a semiconductor such as germanium or gallium arsenide. Instead of the light receiving portions, CPUs, memories, various kinds of sensors or the like may be formed.

Figure 4A:
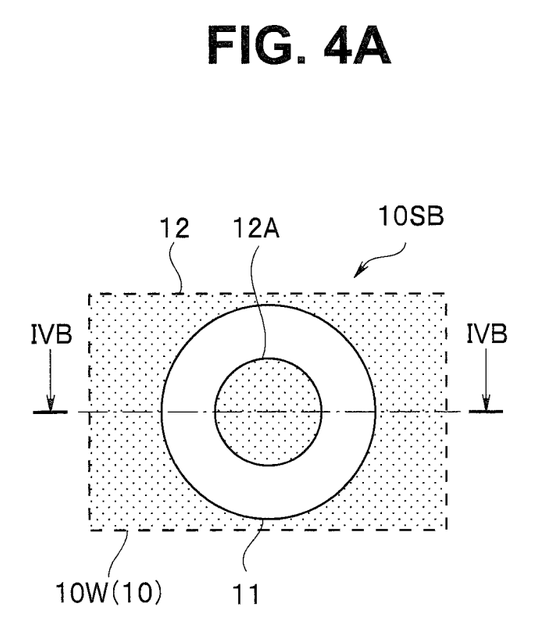
FIG. 4A is a top view of the bonding portion for illustrating a method for manufacturing the first device of the device-bonded body of the first embodiment.
Figure 4B:
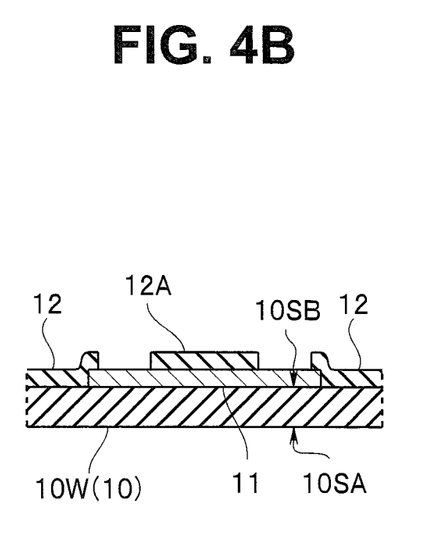
FIG. 4B is a cross-sectional view along a IV-IV line in FIG. 4 for illustrating the method for manufacturing the first device of the device-bonded body of the first embodiment.

As shown in FIGS. 4A and 4B, each of the base electrodes 11 is disposed on the back surface 10SB facing the light receiving surface 10SA of the first wafer 10W. The base electrode 11 made of a conductor such as aluminum is electrically connected to the light receiving portion on the light receiving surface 10SA via a through wire not shown.

A passivation layer 12 is disposed in a manner of covering an outer circumferential portion which is a part of the base electrode 11. A thickness of the passivation layer 12 made of an insulator such as silicon oxide is 1 to 5 μm.

In the device-bonded body 1, a passivation layer 12A in a circular shape is also disposed in a manner of covering a part of the base electrode 11, inside a circular opening of the passivation layer 12. The passivation layer 12 and the passivation layer 12A are simultaneously formed, for example, by a CVD method and separated by being patterned.

For example, an outer diameter of the circular passivation layer 12A is 15 μm, and an outer diameter of the circular opening of the passivation layer 12 surrounding the passivation layer 12A is 40 μm.

Figure 5A:
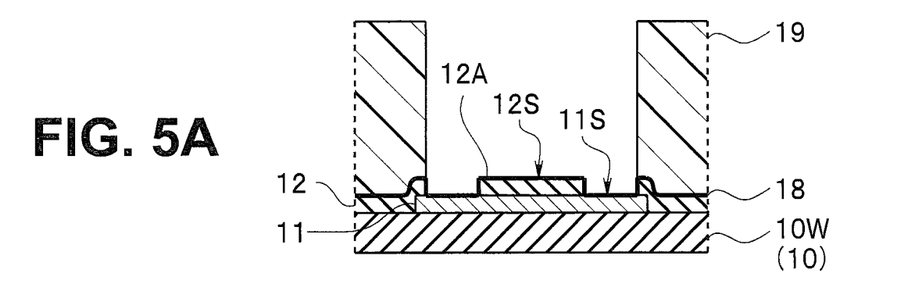
FIG. 5A is a cross-sectional view of the bonding portion for illustrating a method for manufacturing the device-bonded body of the first embodiment.

Next, as shown in FIG. 5A, the seed layer 18 is disposed in a manner of covering the whole surface of the first wafer 10W (the first devices 10), that is, the base electrodes 11, the passivation layer 12 and the passivation layer 12A. For example, a metal layer with a thickness of 0.1 μm is formed by a sputtering method. The seed layer 18 is an electrically conductive base layer for electroplating. On a surface of each bump-disposed portion on the seed layer 18, a center portion 12S is a protrusion higher than an outer circumferential portion 11S because of the circular passivation layer 12A.

Then, a plated mask layer 19 having openings with an inner diameter corresponding to an outer diameter of the bumps 15 are disposed by a photography method. For example, after application of photoresist or film resist, an exposure process and a development process are performed to form the openings. A thickness of the plated mask layer 19 is equal to or higher than a height of the bumps 15.

Figure 5B:
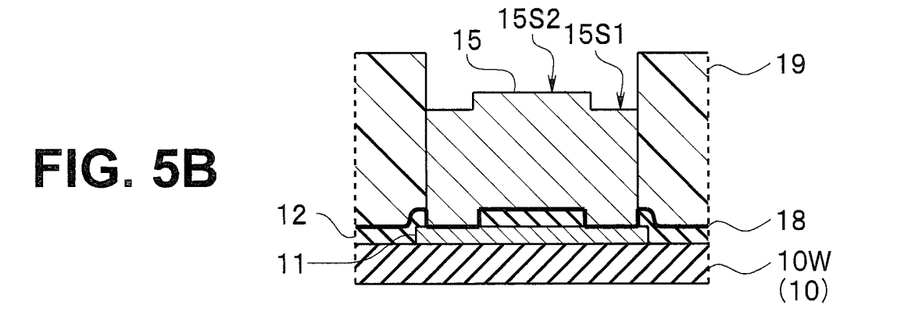
FIG. 5B is a cross-sectional view of the bonding portion for illustrating the method for manufacturing the device-bonded body of the first embodiment.

Next, as shown in FIG. 5B, the bumps 15, for example, made of gold are disposed by an electroplating method. Since a gold plating film isotropically grows, a surface shape of the electroplated film (the bump 15) is the same as a surface shape of the seed layer 18.

That is, as already described, the surface of each of the bumps 15 includes the first area 15S1 and the second area 15S2 higher than the first area 15S1, and the circular second area 15S2 is surrounded by the annular first area 15S1 without a gap.

The shape of the second area 15S2 is almost the same as the shape of the passivation layer 12A disposed below the second area 15S2, and a difference between heights of the first area 15S1 and the second area 15S2 is almost the same as a thickness of the passivation layer 12A.

The bumps 15 may be any electroplated film that isotropically grows. For example, a copper plating film, a nickel plating film or a two-layer plating film of copper/gold is possible.

Figure 5C:
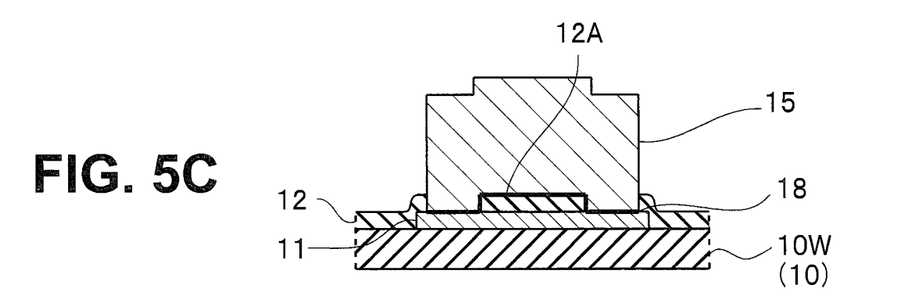
FIG. 5C is a cross-sectional view of the bonding portion for illustrating the method for manufacturing the device-bonded body of the first embodiment.

As shown in FIG. 5C, the plated mask layer 19 is removed by solvent or the like, and the seed layer 18 around the bumps 15 is removed by an etching method or an ion milling method.

Separately, a second wafer 20W including a plurality of second devices 20 is fabricated. Each of the second devices 20 is, for example, a semiconductor device having a signal processing circuit. On the second device 20, the bonding electrodes 21 bonded to the base electrodes 11 (the bumps 15) of the first device 10 are disposed. The bonding electrodes 21 are a conductive pattern made of gold, copper or the like, which is disposed by a plating method, a sputtering method or the like.

Note that the second devices 20 are not limited to semiconductor devices but may be, for example, ceramic wiring boards.

Figure 5D:
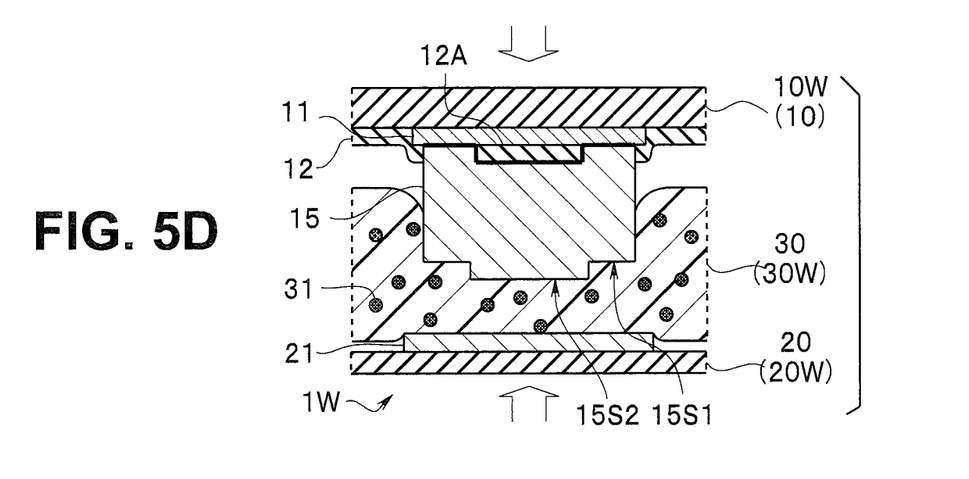
FIG. 5D is a cross-sectional view of the bonding portion for illustrating the method for manufacturing the device-bonded body of the first embodiment.

Then, as shown in FIG. 5D, the first wafer 10W including the plurality of first devices 10 and the second wafer 20W including the plurality of second devices 20 are bonded via the sealing layer 30 made of NCF or NCP by "the first-in method". That is, the base electrodes 11 (the bumps 15) of the first wafer 10W and the base electrodes 11 of the second wafer 20W are aligned, pressure-attached to each other via the sealing layer 30 (30W) and heat-treated.

If the sealing layer 30 is made of NCP, the sealing layer 30 is disposed, for example, on a surface of the second wafer 20W by spin coating or spray coating.

For example, when the surface of the bumps 15 and the surface of the bonding electrodes 21 are made of gold, both are strongly bonded to each other by ultrasound bonding.

A resin component of the sealing layer 30 is thermosetting resin such as epoxy resin, phenoxy resin or phenolic resin.

The filler particles 31 reduce a difference between coefficients of thermal expansion of adhesion surfaces of the first device 10 and the second device 20 and improve reliability of the device-bonded body 1. For example, the filler particles 31 are made of silicon oxide ($SiO_2$), aluminum oxide ($Al_2O_3$), magnesium oxide (MgO) or the like. Note that a shape of the filler particles 31 is not especially limited but may be in any shape such as a spherical shape, an indeterminate shape or a scaly shape.

A particle diameter of the filler particles 31 is 0.01 to 20 μm. The particle diameter is an arithmetic mean value of a maximum particle diameter and is measured by an image analysis method using a microscope, SEM or TEM. If the shape of the filler particles 31 is a shape other than a spherical shape, an average particle diameter means a maximum size. Content of the filler particles 31 is 30 to 70 weight %.

A thickness of the sealing layer 30 is almost the same as the height of the bumps 15.

At the time of bonding, the sealing layer 30 sandwiched between the bumps 15 and the bonding electrodes 21 deforms and spreads around the bumps 15. The surface of each of the bumps 15 forms a protrusion because of the first area 15S1. Therefore, the filler particles 31 do not easily remain between the first area 15S1 of the bump 15 and the bonding electrode 21.

Note that, for example, the height (the second area 15S2) of the bump 15 is 5 to 50 μm, and the outer diameter (the first area 15S1) is 20 to 100 μm. An outer diameter of the second area 15S2 is 30 to 70% of an outer diameter of the first area 15S1. That is, an area of the first area 15S1 is 9 to 50% of an area of the second area. If the area of the first area 15S1 is within the above range, adhesion strength and conductivity between the bumps 15 and the base electrodes 11 can be ensured.

For example, if the outer diameter of the first area 15S1 is 40 μm, and the outer diameter of the second area 15S2 is 15 μm, then an area of a top surface of the bump 15 is 1256 μm². An area of the first area 15S1 in a ring shape, which is not covered by the passivation layer 12A and is in contact with the base electrode 11 (via the seed layer 18) is 1079 μm². That is, the area of the first area 15S1 is 86% of the area of the second area.

Note that it is preferred that the difference between the heights of the first area 15S1 and the second area is 1 to 5 μm, which is 5 to 10% of the height of the bump 15. If the height difference is within the above range, the filler particles 31 do not easily remain, and reliability can be ensured.

A bonded wafer 1W obtained by bonding the first wafer 10W including the plurality of first devices 10 and the second wafer 20W including the plurality of second devices 20 is cut, and the device-bonded body 1 shown in FIG. 1 is fabricated.

Note that though the surface of the second area 15S2 is flat, it is more preferred that the surface is in a protruding shape. Furthermore, the whole outer circumferential portion of the second area 15S2 is in contact with the first area 15S1. That is, the whole side surface 15SS2 of the outer circumferential portion of the second area 15S2 intersects with the surface of the first area 15S1. However, if at least a part of the side surface 15SS2 intersects with the surface of the first area 15S1, the filler particles 31 can be suppressed from being caught in the bonding interface. Though a bonding surface of the bump 15 is circular, the bonding surface may be rectangular.

As described above, the method for manufacturing a device-bonded body of the present embodiment includes a process for disposing the plated bumps 15 on the first devices 10 (the first wafer 10W), a process for disposing the bonding electrodes 21 on the second devices 20 (the second wafer 20W) and a process for bonding the plated bumps 15 of the first devices 10 (the first wafer 10W) and the bonding electrodes 21 of the second devices 20 (the second wafer 20W) via the sealing layer 30 (30W) made of NCF or NCP, the sealing layer 30 (30W) including the filler particles 31 made of inorganic material, the surface of each of the plated bumps 15 including the first area 15S1 and the second area 15S2 higher than the first area 15S1, and at least a part of the side surface of the outer circumferential portion of the second area 15S2 intersecting with the first area 15S1.

Note that it is not practical at all to judge whether the sealing layer of the device-bonded body 1 is fabricated by the first-in method or fabricated by the injection method after bonding because appropriate measurement and analysis means do not exist.

<Modifications of First Embodiment>

Next, modifications of the first embodiment will be described. Since device-bonded bodies of the modifications are similar to the device-bonded body 1 of the first embodiment and have the same effects, a same component will be given a same reference numeral, and description of the component will be omitted.

<Modification 1>

Figure 6A:
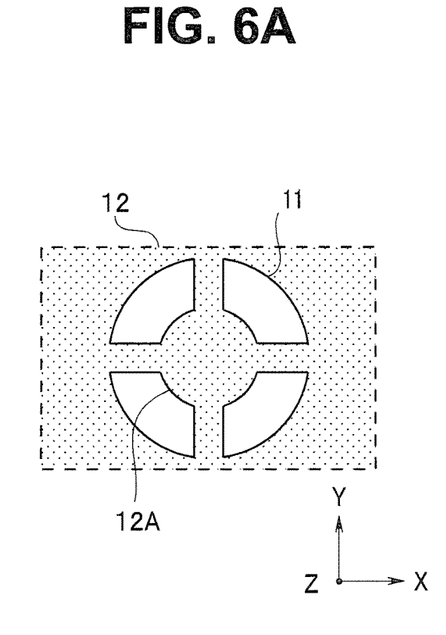
FIG. 6A is a top view of a bonding portion for illustrating a method for manufacturing a first device of a device-bonded body of a modification 1 of the first embodiment.
Figure 6B:
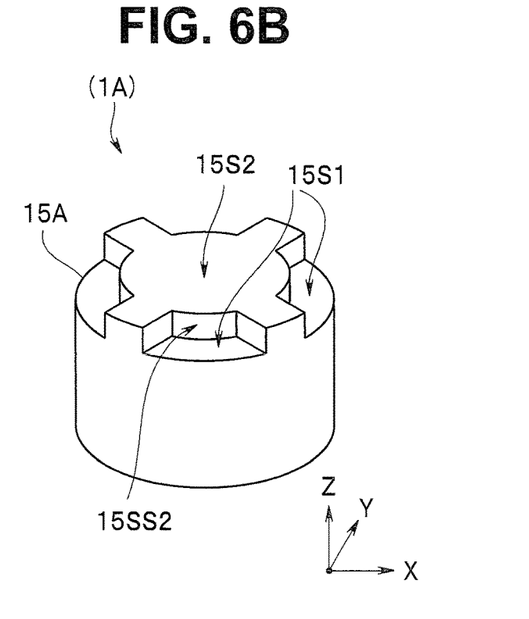
FIG. 6B is a perspective view of a bump of the device-bonded body of the modification 1 of the first embodiment.

As shown in FIG. 6A, in a device-bonded body 1A of a modification 1, each passivation layer 12A and the surrounding passivation layer 12 are connected. Therefore, as shown in FIG. 6B, the first area 15S1 of each bump 15A includes four areas, the second area 15S2 existing among the four areas. That is, four positions of the side surface 15SS2 of the outer circumferential portion of the second area 15S2 intersect with the surface of the first area 15S1.

An area in contact with the base electrode 11 is larger on the bump 15A than on the bump 15. Further, since the four positions of the outer circumferential portion of the passivation layer 12A are connected to the surrounding passivation layer 12, the passivation layer 12A does not easily detach. Since bonding strength of the bumps 15A is high, reliability of the device-bonded body 1A is higher than the device-bonded body 1.

<Modification 2>

Figure 7A:
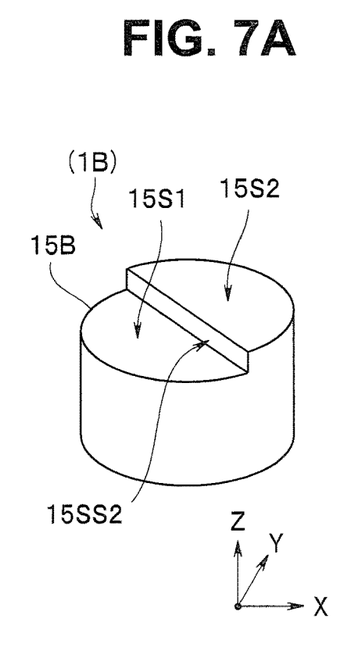
FIG. 7A is a perspective view of a bump of a device-bonded body of a modification 2 of the first embodiment.

As shown in FIG. 7A, a surface of each bump 15B of a device-bonded body 1B of a modification 2 is in a circular shape including the first area 15S1 in an almost semicircular shape and the second area 15S2 in an almost semicircular shape. That is, the side surface 15SS2 corresponding to a chord part of the outer circumferential portion of the second area 15S2 in the almost semicircular shape intersects with the surface of the first area 15S1. The area of the first area 15S1 is 50% of the area of the second area.

On all of the bumps 15, 15A and 15B of the first embodiment, the modification 1 and the modification 2, at least a part of the side surface of the outer circumferential portion of the second area 15S2 intersects with the surface of the first area 15S1. Therefore, the filler particles 31 do not easily remain between the first area 15S1 of each of the bumps 15, 15A and 15B and the bonding electrode 21.

Note that if at least a part of the outer circumferential portion of the second area 15S2 is in contact with the first area 15S1, the shapes of the first area 15S1 and the second area 15S2 are not limited to the shapes illustrated on the bumps 15, 15A and 15B but can be appropriately selected.

<Modification 3>

In a device-bonded body 1C of a modification shown in FIGS. 7B to 9, a passivation layer 12B and a second bump 25B are also disposed for each of the bonding electrodes 21 of the second device 20. A configuration of the second bump 25B is almost the same as the bump 15B shown in FIG. 7A.

Figure 7B:
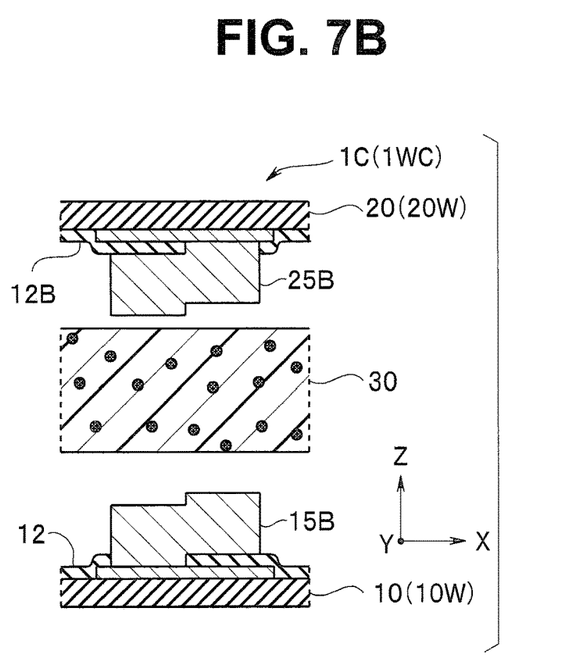
FIG. 7B is a cross-sectional exploded view of a bonding portion of a device-bonded body of a modification 3 of the first embodiment.
Figure 8:
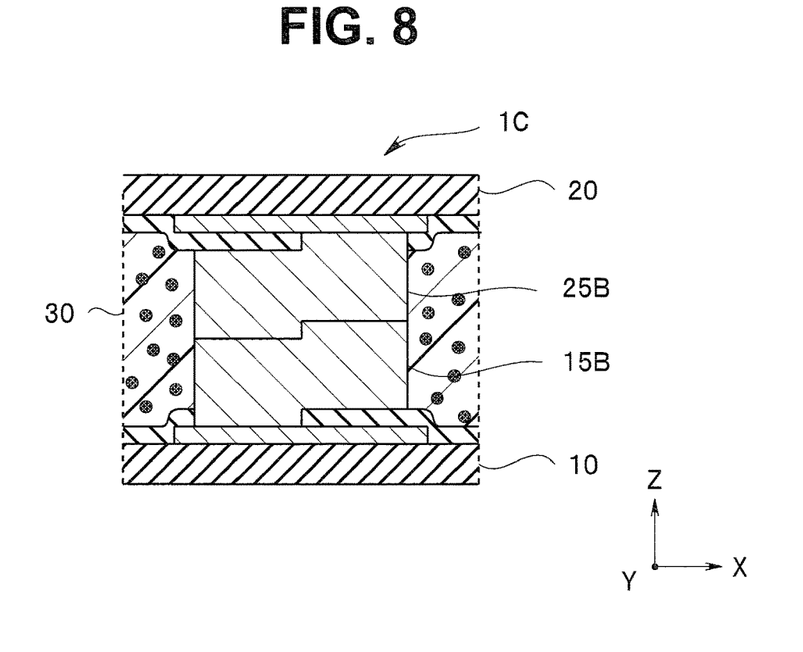
FIG. 8 is a cross-sectional view of the bonding portion of the device-bonded body of the modification 3 of the first embodiment.
Figure 9:
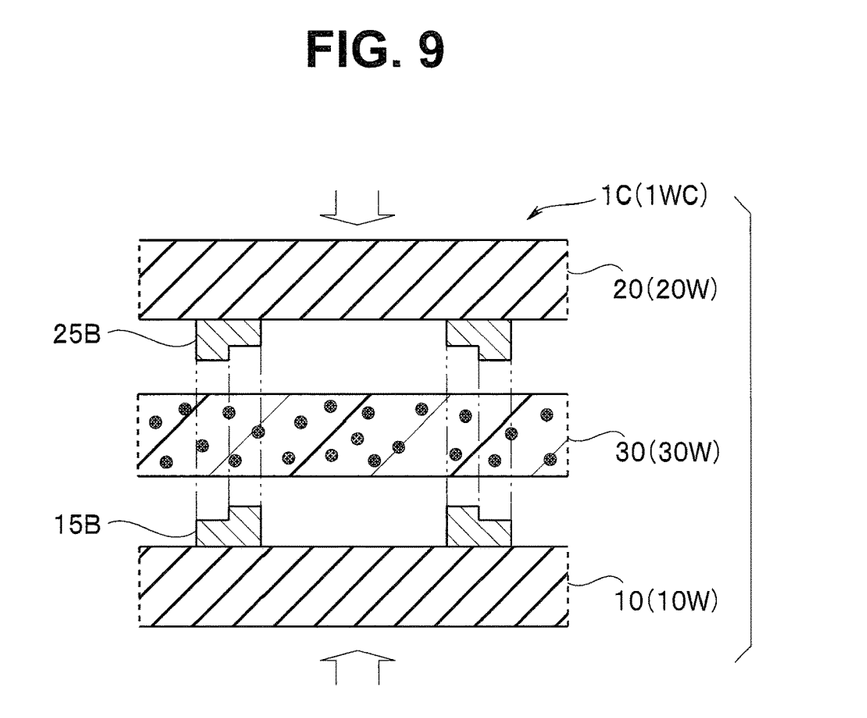
FIG. 9 is a cross-sectional exploded view of the device-bonded body of the modification 3 of the first embodiment.

By the first bumps 15B and the second bumps 25B being mutually fitted, alignment between the first wafer 10W (the first devices 10) and the second wafer 20W (the second devices 20) is automatically performed.

In the case of the device-bonded body 1C, alignment at the time of fabricating a bonded wafer 1WC is easy.

Note that, it goes without saying that, in the device-bonded bodies 1A to 1C in the modifications 1 to 3, the first device 10 may be an image pickup device.

Second Embodiment

Figure 10:
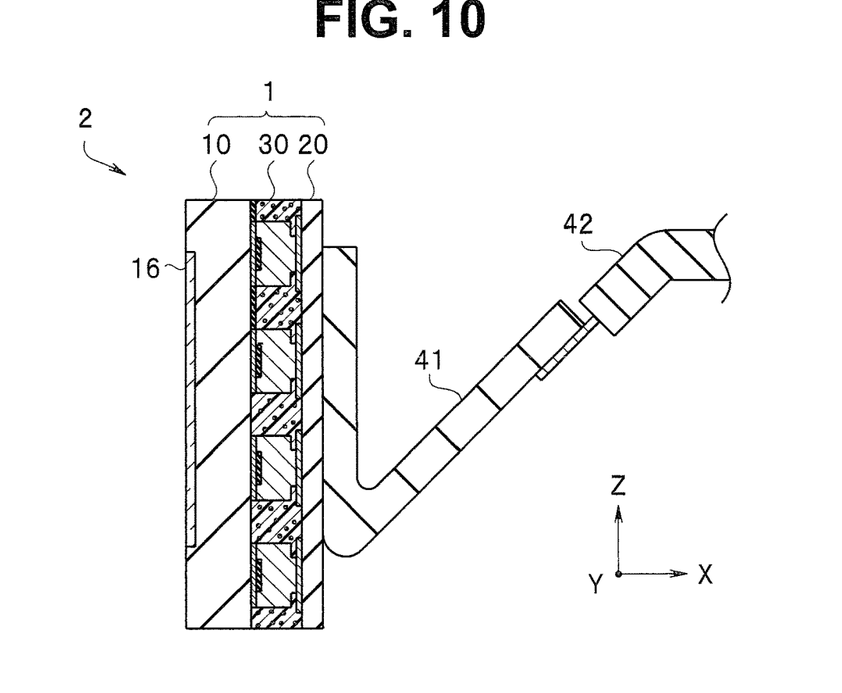
FIG. 10 is a cross-sectional view of an image pickup module of a second embodiment.

As shown in FIG. 10, an image pickup module 2 of a second embodiment has the device-bonded body 1 in which the first device 10 is an image pickup device, a wiring board 41 connected to the device-bonded body 1, and a signal cable 42 connected to the wiring board 41.

On the light receiving surface 10SA of the first device 10, the light receiving portion 16 is formed. A signal outputted by the light receiving portion 16 is transmitted to the bonding electrodes 21 of the second device 20 via through wires (not shown), the base electrodes 11 and the bumps 15. The signal is transmitted to the wiring board 41 bonded to the back surface via through wires (not shown) of the second device 20 and further transmitted to the signal cable 42.

In the image pickup module 2, the first device (the image pickup device) and the second device 20 are bonded by a flip chip method via the characteristic bumps 15, 15A or 15B. Therefore, the image pickup module 2 is easy to manufacture and is highly reliable because the sealing layer 30 by the first-in method using NCF or NCP is provided.

Third Embodiment

Figure 11:
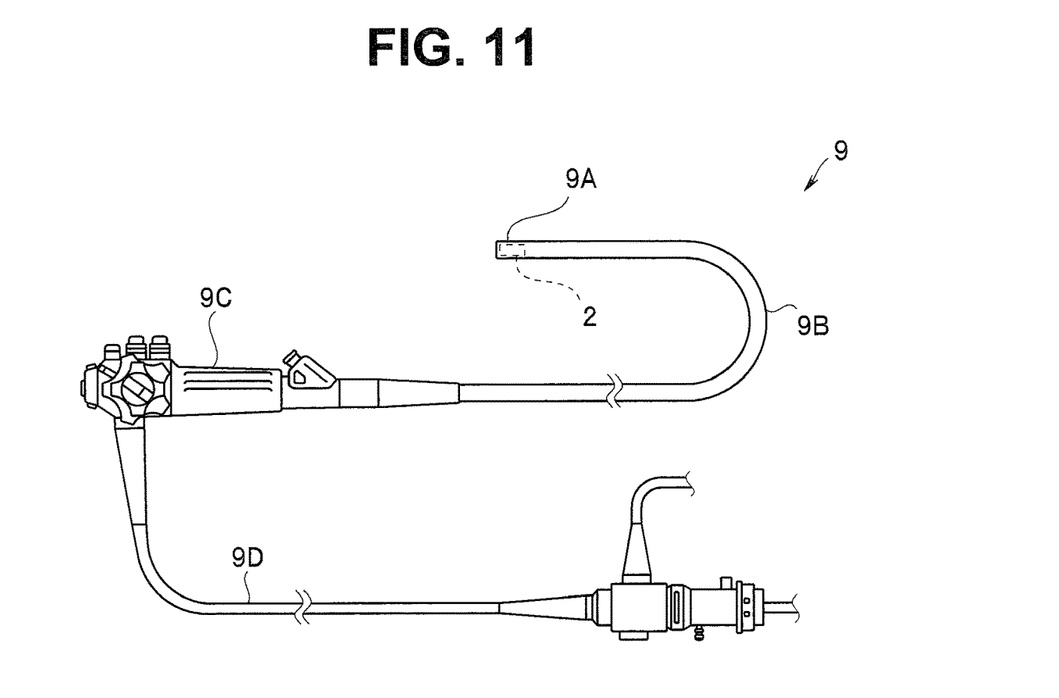
FIG. 11 is a perspective view of an endoscope of a third embodiment.

As shown in FIG. 11, an endoscope 9 of a third embodiment is provided with the image pickup module 2. That is, the endoscope 9 is provided with an insertion portion 9B in which the image pickup module 2 is accommodated in a rigid distal end portion 9A, a grasping portion 9C disposed on a rear portion of the insertion portion 9B and a universal cord 9D extending from the grasping portion 9C. In the universal cord 9D, the signal cable 42 connected to the image pickup module 2 is inserted.

The endoscope 9 is highly reliable because the highly reliable image pickup module 2 is provided.

The present invention is not limited to the embodiments, modifications and the like described above, but various changes, alterations and the like are possible within a range not changing the spirit of the present invention.

What is claimed is:

1. A device-bonded body comprising:
   a first device where a plated bump is disposed;
   a second device where a bonding electrode bonded to the plated bump is disposed; and
   a sealing layer made of NCF or NCP, the sealing layer being disposed between the first device and the second device and including filler particles made of inorganic material, wherein
   a surface of the plated bump includes a first area and a second area higher than the first area,
   at least a part of a side surface of an outer circumferential portion of the second area intersects with a surface of the first area,
   the plated bump is made of an electroplated film formed on a base electrode and a passivation layer covering a part of the base electrode, and
   a shape of the second area is same as a shape of the passivation layer disposed below the second area, and a difference between heights of the first area and the second area is same as a thickness of the passivation layer.

2. The device-bonded body according to claim 1, wherein the outer circumferential portion of the second area is surrounded by the first area in an annular shape without a gap.

3. The device-bonded body according to claim 1, wherein the first area includes a plurality of areas, the second area existing among the plurality of areas.

4. The device-bonded body according to claim 1, wherein the surface of the plated bump is in a circular shape including the first area in an almost semicircular shape and the second area in an almost semicircular shape.

5. The device-bonded body according to claim 1, wherein
a second bump is disposed on the bonding electrode of the second device, and
the plated bump, which is a first bump, and the second bump are mutually fitted.

6. An image pickup module comprising:
a device-bonded body;
a wiring board connected to the device-bonded body; and
a signal cable connected to the wiring board, wherein the device-bonded body comprises:
a first device where a plated bump is disposed, the first device being an image pickup device;
a second device where a bonding electrode bonded to the plated bump is disposed; and
a sealing layer made of NCF or NCP, the sealing layer being disposed between the first device and the second device and including filler particles made of inorganic material,
a surface of the plated bump includes a first area and a second area higher than the first area,
at least a part of a side surface of an outer circumferential portion of the second area intersects with a surface of the first area,
the plated bump is made of an electroplated film formed on a base electrode and a passivation layer covering a part of the base electrode, and
a shape of the second area is same as a shape of the passivation layer disposed below the second area, and a difference between heights of the first area and the second area is same as a thickness of the passivation layer.

7. An endoscope comprising an image pickup module, the image pickup module comprising: a device-bonded body, a wiring board connected to the device-bonded body and a signal cable connected to the wiring board, wherein
the device-bonded body comprises:
a first device where a plated bump is disposed, the first device being an image pickup device;
a second device where a bonding electrode bonded to the plated bump is disposed; and
a sealing layer made of NCF or NCP, the sealing layer being disposed between the first device and the second device and including filler particles made of inorganic material,
a surface of the plated bump includes a first area and a second area higher than the first area,
at least a part of a side surface of an outer circumferential portion of the second area intersects with a surface of the first area,
the plated bump is made of an electroplated film formed on a base electrode and a passivation layer covering a part of the base electrode, and
a shape of the second area is same as a shape of the passivation layer disposed below the second area, and a difference between heights of the first area and the second area is same as a thickness of the passivation layer.

8. A method for manufacturing a device-bonded body comprising:
disposing a plated bump made of an electroplated film on a base electrode and a passivation layer covering a part of the base electrode of a first device;
disposing a bonding electrode on a second device; and
bonding the plated bump of the first device and the bonding electrode of the second device via a sealing layer made of NCF or NCP, the sealing layer including filler particles made of inorganic material, wherein
a surface of the plated bump includes a first area and a second area higher than the first area,
a shape of the second area is same as a shape of the passivation layer disposed below the second area, and a difference between heights of the first area and the second area is same as a thickness of the passivation layer, and
at least a part of a side surface of an outer circumferential portion of the second area intersects with a surface of the first area.

* * * * *